United States Patent [19]

Cherry et al.

[11] 4,228,074
[45] Oct. 14, 1980

[54] AZETIDINONE DERIVATIVES

[75] Inventors: Peter C. Cherry, South Harrow; Christopher E. Newall, Ealing; Nigel S. Watson, Greenford, all of England

[73] Assignee: Glaxo Laboratories Limited, Greenford, England

[21] Appl. No.: 831,549

[22] Filed: Sep. 8, 1977

[30] Foreign Application Priority Data

Sep. 9, 1976 [GB] United Kingdom ............... 37444/76
Sep. 9, 1976 [GB] United Kingdom ............... 37481/76

[51] Int. Cl.² .................. C07D 205/08; C07D 405/12; C07D 413/04; C07D 417/04
[52] U.S. Cl. ............................ 260/239 A; 260/245.3; 260/345.8 R; 544/60; 544/111; 546/133; 546/208; 546/275
[58] Field of Search ................ 260/239 A, 345.8 R; 546/133, 208, 275; 544/60, 111

[56] References Cited

U.S. PATENT DOCUMENTS 4,018,782  4/1977  Wolfe .......................... 260/239 A

OTHER PUBLICATIONS

Nobats et al., Basic Principles of Organic Chemistry (1964), p. 484.

Primary Examiner—Mark L. Berch
Attorney, Agent, or Firm—Bacon & Thomas

[57] ABSTRACT

β-Lactam compounds of the formula (I)

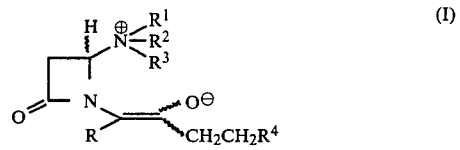

(wherein R represents an esterified carboxyl group, $\overset{\oplus}{N}R^1R^2R^3$ represents the residue of a nitrogen base, and $R^4$ represents a hydrogen atom, a hydroxyl group or acylated or etherified hydroxyl group or the residue of a sulphur nucleophile) are disclosed, together with processes for their preparation. The compounds are valuable intermediates for the preparation or purification of further β-lactam compounds having β-lactamase inhibitory activity.

7 Claims, No Drawings

AZETIDINONE DERIVATIVES

This invention relates to new antibiotic intermediates and to a process for their production.

In our German OLS No. 26 04 697 we have described the isolation, from fermentations of *Streptomyces clavuligerus*, of clavulanic acid and salts thereof in pure form.

The bicyclic compounds in this specification are named with reference to "clavam"; the name being given to the parent heterocycle of formula A

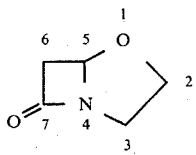

by analogy with the term "cepham" used in the naming of cephalosporin compounds in J. Amer. Chem. Soc, 1962, 84, 3400.

We have now been able to prepare monocyclic betaines related to clavulanic acid and according to one aspect of the invention, we provide compounds of the formula (I)

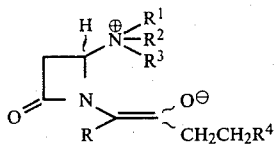

wherein R represents an esterified carboxyl group; $N^{\oplus}R^1R^2R^3$ represents the residue of a nitrogen base; and $R^4$ represents a hydrogen atom, a hydroxyl group, an etherified hydroxyl group, an acylated hydroxyl group or the residue of a sulphur nucleophile.

$R^1$, $R^2$ and $R^3$, which may be the same or different, may each represent an aliphatic, araliphatic or aromatic group, e.g. alkyl groups having up to eight carbon atoms; aralkyl groups having up to six carbon atoms in the alkyl portion or aryl groups, such aryl and aralkyl groups desirably being monocyclic; cycloaliphatic e.g. $C_{3-7}$ cycloalkyl groups, or two of $R^1$, $R^2$ and $R^3$ may form, together with the nitrogen atom to which they are attached, a five-, six- or seven-membered heterocyclic ring optionally containing a further heteroatom e.g. an oxygen, nitrogen or sulphur atom as in a piperidino, morpholino or thiamorpholino group, or $R^1$, $R^2$ and $R^3$ together may form part of a heterocyclic aromatic ring e.g. a pyridinium or collidinium group, or a polycyclic e.g. a bicyclic, heterocyclic system e.g. a quinuclidino group.

$R^1$, $R^2$ and $R^3$ are each preferably a $C_{1-6}$ alkyl group, such as a methyl, ethyl, propyl or butyl group. Trimethylammonium and triethylammonium groups are especially preferred.

The invention further includes acid-addition salts of the compounds of formula (I). Such salts may be formed with either organic or inorganic acids. Suitable organic acids include carboxylic acids, e.g. citric, formic, tartaric and acetic acids, or sulphonic acids e.g. p-toluene sulphonic acid; suitable inorganic acids include mineral acids e.g. nitric, hydrochloric, sulphuric and perchloric acids.

The compounds of the invention will in general be mixtures of the azetidin-2-one 4-position epimers and in solution will also constitute a mixture of geometric isomers around the double-bond in the 1-position side chain due to the possibility of equilibration arising from keto-enol tautomerism, although the crystalline material will normally exist as one or the other of the possible E and Z isomers.

The group $R^4$ may represent an etherified hydroxyl group $—OR^5$, wherein $R^5$ is a substituted or unsubstituted hydrocarbyl group, e.g. an aliphatic, araliphatic or aromatic group or a C-attached heterocyclic group. Thus, for example, $R^5$ may be an unsubstituted alkyl, alkenyl or alkynyl group, which may contain 1–6 carbon atoms, or such an alkyl group carrying a substituted hydroxy, acyl (e.g. $C_{2-6}$ alkanoyl), carboxyl, esterified carboxyl (e.g. $C_{2-6}$ alkoxycarbonyl) or cyano group; a hydroxyalkyl group having 2–6 carbon atoms; an aralkyl group which may have 1–6 carbon atoms in the alkyl portion or an aryl group, such aryl and aralkyl groups preferably being monocyclic and optionally carrying one or more nitro, halo or $C_{1-4}$ alkoxy substituents; a cycloalkyl group, which may have 3–7 carbon atoms or a carbon-attached saturated or unsaturated 5–7 membered heterocyclic ring containing, for example, an oxygen atom, such cycloalkyl or heterocyclic rings optionally carrying a $C_{1-4}$ alkoxy group, preferably attached to the ether-linked carbon atom.

Representative groups $R^5$ include methyl, ethyl, propyl, isopropyl, butyl, allyl, propargyl, hydroxyethyl, 1-ethoxyethyl, acetonyl, 4-nitrobenzyl, cyanomethyl, carboxyethyl, ethoxycarbonylmethyl, phenyl, benzyl, phenethyl, cyclohexyl, 1-methoxycyclohexyl and tetrahydropyranyl.

Substituted hydroxy groups as referred to above include acylated and etherified hydroxy groups. In general, acylated hydroxy groups may have the formula $R^6CO_2$ where $R^6$ is a hydrocarbyl group as defined for $R^5$, relatively simple $R^6$ groups such as $C_{1-4}$ alkyl e.g. methyl being preferred, while etherified hydroxy groups may have the formula $R^6O$, simple $R^6$ groups such as $C_{1-4}$ alkyl, e.g. methyl or ethyl, again being preferred.

$R^5$ may also be a silyl group having up to 24 carbon atoms, which may carry three hydrocarbyl groups. The groups, which may be the same or different, may be selected from alkyl, alkenyl, cycloalkyl, aralkyl and aryl groups. Such groups will preferably be $C_{1-4}$ alkyl, e.g. methyl, ethyl, propyl or butyl groups. Representative silyl groups include trimethylsilyl and t-butyldimethylsilyl groups.

The group $R^4$ may further represent an acylated hydroxyl group $—OR^7$ wherein $R^7$ preferably represents an acyl group $R^8CO—$ wherein $R^8$ is an aliphatic, araliphatic or aromatic group, for example a $C_{1-8}$ alkyl, $C_{2-8}$ alkenyl, $C_{2-8}$ alkynyl, $C_{3-12}$ cycloalkyl, $C_{4-15}$ aryl-$C_{1-6}$-alkyl or $C_{4-15}$ aryl group, which may be substituted, for example, by one or more hydroxyl, $C_{1-4}$ alkoxy, phenoxy or cyano groups, or an amino or mono- or di-substituted amino group, or a carboxyl or esterified carboxyl group. The group $R^8$ may also represent an amino or mono- or di-substituted amino group, thus making the group $R^4$ a carbamoyloxy group which may, for example, be represented as $—O.CO.NR^9R^{10}$, where $R^9$ and $R^{10}$, which may be the same or different, are hydrogen; $C_{1-5}$ alkyl or $C_{2-6}$ alkanoyl, which may be substituted by, for example, halogen; aralkyl e.g. benzyl; or aryl e.g. phenyl groups, or $R^9$ and $R^{10}$ may together with the nitrogen atom to which they are attached form a heterocyclic ring preferably having 5-7 ring members which may optionally contain another heteroatom e.g. a nitrogen, oxygen or sulphur atom. $R^4$ may additionally be represented as O.CS.NHR$^9$ where $R^9$ is as defined above other than hydrogen.

Representative $R^8$ groups include methyl, ethyl, propyl, isopropyl, butyl, amyl, allyl, propenyl, propargyl, cyclopentyl, cyclohexyl, cycloheptyl, adamantyl, benzyl, thienylmethyl, phenyl, thienyl, amino, methylamino, anilino, α-benzyloxycarbonylbenzyl, α-phenoxycarbonylbenzyl, aminomethyl or α-aminobenzyl groups.

The group $R^4$ may also represent the residue of a sulphur nucleophile, for example an acylthio or thioacylthio group, a thioether group or a sulphone or sulphoxide derivative of said thioether group or a thiol group. In general these residues may be represented by the formulae —SH, —SR$^{11}$, —SO.R$^{11}$ or —SO$_2$R$^{11}$ (where $R^{11}$ is an aliphatic, araliphatic, aromatic or heterocyclic group) or by —SC=Y.R$^{12}$ (where Y is O or S and $R^{12}$ is a group as defined above for $R^{11}$ or a group OR$^{11}$ or SR$^{11}$, where $R^{11}$ is as defined above, or a group NR$^{13}$R$^{14}$, where $R^{13}$ and $R^{14}$, which may be the same or different, are hydrogen atoms or aliphatic, araliphatic or aromatic groups or together with the nitrogen atom to which they are attached represent a heterocyclic ring).

Thus for example, $R^{11}$, $R^{12}$, $R^{13}$ and $R^{14}$ may be alkyl, alkenyl or alkynyl groups, which may contain 1-6 carbon atoms; aralkyl groups which may have 1-6 carbon atoms in the alkyl portion or aryl groups, such aryl and aralkyl groups preferably being monocyclic; cycloalkyl groups, which may have 3-7, preferably 5 or 6 carbon atoms; or carbon-attached 5-7 membered heterocyclic rings containing one or more heteroatoms such as nitrogen, sulphur or oxygen, and may carry one or more alkyl groups which may have 1-6 carbon atoms. Such groups may themselves carry substituents such as hydroxyl or substituted hydroxyl, carboxyl or substituted carboxyl, amino or substituted amino, or cyano groups.

Representative groups $R^{11}$ include methyl, ethyl, propyl, butyl, allyl, propargyl, 2-aminoethyl, cyanomethyl, hydroxyethyl, ethoxyethyl, phenyl, benzyl, cyclohexyl and pyridyl.

Representative groups $R^{12}$.C=Y.— include ethoxythiocarbonyl, carbamoyl, thiocarbamoyl, dimethylthiocarbamoyl, thiobenzoyl, benzoyl, thiacetyl and acetyl. Where NR$^{13}$R$^{14}$ represents a heterocyclic ring, this may for example, contain 5-7 ring atoms, including one or more other heteroatoms e.g. nitrogen, oxygen or sulphur atoms, and may be, for example, a piperidino, piperazino, morpholino or thiamorpholino ring.

Substituted hydroxy groups include acylated and etherified hydroxy groups as referred to above. Substituted carboxyl groups may have the formula COOR$^{15}$, where $R^{15}$ is an aliphatic, araliphatic or aromatic group, while substituted amino groups may have the formula NR$^{13}$R$^{14}$ as defined above, one of $R^{13}$ and $R^{14}$ being other than hydrogen. Preferred groups $R^{13}$, $R^{14}$ and $R^{15}$ are C$_{1-4}$ alkyl groups e.g. methyl.

The compounds of the invention are esters wherein the group R represents an esterified carboxyl group which is conveniently derived from an alcohol (aliphatic or araliphatic), a phenol or a stannanol. Such an alcohol, phenol or stannanol used to esterify the carboxyl group preferably contains not more than 24 carbon atoms.

Thus, the group R may be represented as COOR$^{16}$ wherein $R^{16}$ represents a straight or branched unsubstituted or substituted alkyl or alkenyl group, preferably having from 1-8 carbon atoms, for example a methyl, ethyl, propyl or isopropyl, butyl, sec-butyl, tert-butyl or allyl group, desirable substituents being for example, alkoxy e.g. methoxy; halogen i.e. fluorine, chlorine, bromine or iodine; cyano; acyloxy, e.g. alkanoyloxy, such as acetoxy or pivaloyloxy; acyl e.g. p-bromobenzoyl and alkoxycarbonyl e.g. ethoxycarbonyl;

an aralkyl group having up to 20 carbon atoms especially an arylmethyl group e.g. a benzyl or substituted benzyl group, suitable ring substituents being halo e.g. chloro; nitro e.g. o- or p-nitro; sulphonyl; cyano; alkyl e.g. p-methyl or alkoxy e.g. p-methoxy; a diphenylmethyl, or triphenylmethyl group or a fur-2-ylmethyl, thien-2-ylmethyl or pyridylmethyl group, the heterocyclic groups of which may also be substituted e.g. by a lower alkyl group, preferably methyl;

an aryl group having up to 12 carbon atoms e.g. a phenyl or substituted phenyl group, suitable substituents being halo e.g. chloro; nitro e.g. o- or p-nitro; cyano; alkyl e.g. p-methyl or alkoxy e.g. p-methoxy;

a cycloalkyl group containing not more than 12 carbon atoms, e.g adamantyl;

a heterocyclic group containing not more than 12 carbon atoms, the heteroatom being for example oxygen, as in the tetrahydropyranyl or phthalidyl groups;

or a stannyl group having up to 24 carbon atoms for example a stannyl group carrying three substituents which may be the same or different selected from alkyl, alkenyl, aryl, aralkyl, cycloalkyl, alkoxy, or aralkoxy groups. Such groups will include methyl, ethyl, propyl, n-butyl, phenyl and benzyl groups.

The esters which will be used when it is desired ultimately to prepare a carboxylic acid or salt thereof will desirably be those which may be cleaved under conditions which will not result in undesirable side reactions. Suitable esters for this purpose include the arylmethyl esters, for example p-nitrobenzyl and benzhydryl esters; such esters may be cleaved by reduction, for example by hydrogenolysis e.g. on a noble metal catalyst.

The compounds of the invention are useful intermediates in the synthesis or purification of further β-lactam compounds, for example compounds having the formula (II)

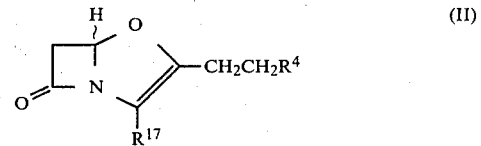

(II)

wherein $R^4$ is as defined above and $R^{17}$ represents a carboxyl or esterified carboxyl group and salts of the compounds in which $R^{17}$ is a carboxyl group. Such compounds are described and claimed in our copending U.S. application Ser. No. 831,548, filed Sept. 8, 1977.

Compounds of formula (II) possess the ability to inhibit β-lactamase enzymes produced by both gram-positive and gram-negative organisms such as strains of *Proteus mirabilis, Staphylococcus aureus, Escherichia coli, Proteus morganii, Klebsiella aerogenes, Salmonella typhimurium, Shigella sonnei, Haemophilus influenzae, Enterobacter cloacae, Pseudomonas aeruginosa,* indolepositive Proteus species and *Bacteroides fragilis.* Thus compounds of formula (II) have the ability to protect β-lactamase susceptible β-lactam antibiotics from β-lactamase hydrolysis.

The compounds of formula (I) have also been found to be valuable in the purification of esters of formula (II) above since they can provide crystalline material from which the esters of formula (II) may readily be regenerated in a high state of purity.

The compounds of formula (II) may readily be prepared from compounds of formula (I) or their acid addition salts by removal of the group $NR^1R^2R^3$. Such removal may, for example, be achieved by heating, e.g. at 50°–100° C., preferably under reflux, in a suitable liquid medium. Where an acid addition salt of a compound of formula (I) is used, it may be advantageous to include one equivalent of an acid binding agent. The liquid medium will preferably be a low-boiling inert liquid e.g. an ester, such as ethyl acetate, a halogenated hydrocarbon such as 1,2-dichloroethane or chloroform, a hydrocarbon such as benzene, a ketone such as acetone or an ether such as tetrahydrofuran. Higher boiling liquids such as amides, e.g. dimethyl formamide can also be used. Where an acid of formula (II) or a salt thereof is required, this may be prepared by cleavage of an ester initially produced.

Certain compounds of formula (I) are also useful in the production of diene esters of formula (III)

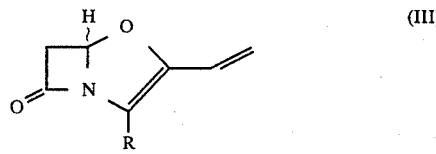

(wherein R represents an esterified carboxyl group) as more particularly described hereinafter.

Such dienes are described in our copending U.S. application Ser. No. 809,915, filed June 24, 1977, and are valuable intermediates in the preparation of, inter alia, antibiotic and β-lactamase inhibitory thio-derivatives of clavulanic acid of the type described in our German OLS No. 2708330; these diene esters have also been reported as possessing β-lactamase inhibitory activity.

The compounds of the invention may conveniently be prepared by the reaction of a compound of formula (II) wherein $R^{17}$ is an esterified carboxyl group or a compound of formula (IV)

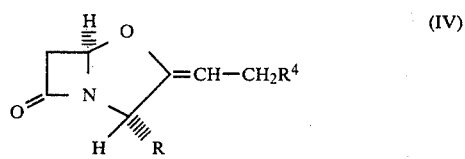

wherein R and $R^4$ are as defined above, with an amine of formula $R^1R^2R^3N$ (wherein $R^1$, $R^2$ and $R^3$ are as described above) whereby the desired compound of formula (I) is obtained.

Where $R^4$ is a group which may be readily eliminated e.g. a dichloroacetoxy group, there will be a tendency for elimination to occur in the presence of the base, whereby a diene of formula (III) is produced. Where a compound of formula (I) is required in which $R^4$ represents such a readily eliminatable group, these are conveniently prepared from a compound of formula (I) in which $R^4$ is hydroxy.

In general, the conversion of a compound of formula (II) into a compound of formula (I) can be effected using a weaker base than is required for the conversion of a compound of formula (IV). Thus, for example, an aromatic tertiary base such as pyridine can be used successfully for conversion of a compound of formula (II), whereas a stronger base such as triethylamine is generally required for the conversion of a compound of formula (IV).

On the other hand a compound of formula (IV) may be converted into a compound of formula (I) wherein $NR^1R^2R^3$ is the residue of a weak base such as pyridine by reaction with the weak base in the presence of a catalytic quantity of a strong base.

Use of the simpler trialkylamines, however, e.g. having 1–6 carbon atoms in each alkyl group, especially methyl, ethyl, propyl or butyl groups is preferred and trimethylamine and triethylamine are especially preferred for both series of compounds.

Reaction may be carried out in a suitable non-hydroxylic solvent e.g. an ester such as ethyl acetate, an amide such as dimethylformamide, a halogenated hydrocarbon such as dichloromethane or chloroform, a ketone such as acetone or an ether such as diethyl ether. Alternatively, the amine itself may serve as the solvent. It is preferred to use ethyl acetate or dimethylformamide as the solvent.

Reaction may be carried out at a temperature of from −40° C. to +30° C., a temperature of from +10° to +20° C. being preferred; in some cases subsequent cooling may be advantageous in order to facilitate the isolation of a product of formula (I) in a pure state.

The compounds of formula (I) may readily be separated from the reaction mixture by conventional separation and isolation techniques. As mentioned above, the compounds of the invention are betaines and normally crystallise readily from some of the above solvents. It is often the case that the compounds of the invention crystallise out from the reaction solution on allowing it to stand over a period of time but if an oil should be formed, for example, solid may often readily be obtained by simple purification means e.g. trituration with fresh solvent. For the preparation of acid addition salts of the compounds of formula (I) it is preferred to redissolve the isolated betaine in a suitable solvent such as dimethylformamide or water and add one equivalent of the appropriate acid.

The compounds of formula (IV) whence the compounds of the invention may be prepared may themselves be prepared in a variety of ways from clavulanic acid or its salts or esters and reactive derivatives thereof, such as halo derivatives (i.e. compounds of formula (IV) in which $R^4$ is a halogen atom). These halo derivatives are described in our German OLS No. 2657081.

The compounds of formula (IV) wherein $R^4$ is a hydrogen atom may be prepared by catalytic hydrogenolysis as described in our German OLS No. 2657081 and South African Pat. No. 76/1953.

Compounds of formula (IV) wherein $R^4$ represents an etherified hydroxyl group may be prepared by etherification of an ester of clavulanic acid as described in our German OLS No. 2657048 and South African Pat. No. 76/5560.

Silyl ethers may be prepared using the appropriate silyl halide e.g. trimethyl silyl chloride or t-butyl-dimethyl silyl chloride.

Compounds of formula (IV) wherein $R^4$ represents an acylated hydroxyl group $-OCOR^8$ wherein $R^8$ is as defined above may be prepared by reaction of clavulanic acid or an ester thereof with a compound of formula $R^8COY$ (wherein $R^8$ is as defined above and Y represents a hydroxyl group or a readily eliminatable substituent). The reaction will desirably be effected under mild conditions in order to prevent rupture of the bicyclic nucleus. The use of neutral or mild acidic or basic conditions, therefore, at temperatures between $-70°$ C. and $+35°$ C. is preferred. Where a carboxylic acid is initially produced this may be converted into an ester by the methods described hereinafter.

Thus, clavulanic acid or an ester thereof may be reacted with a reactive derivative of a carboxylic acid e.g. a halide or anhydride, for example, an acid chloride. In this case reaction may be effected using either the free antibiotic carboxylic acid or, more preferably, an ester thereof, desirably under mild basic conditions e.g. in the presence of a pyridine base in a solvent such as an ether e.g. tetrahydrofuran or dioxan, or ester e.g. ethyl acetate or halogenated hydrocarbon e.g. methylene chloride or a substituted amide e.g. dimethylacetamide.

Alternatively, a mono-N-substituted carbamate or thiocarbamate may be prepared using an isocyanate of formula $R^9NCO$ or an isothiocyanate of formula $R^9NCS$ in which $R^9$ is as defined above. The reaction will preferably be carried out by allowing an ester of clavulanic acid to react with an isocyanate or isothiocyanate, optionally in the presence of a mild organic base e.g. pyridine, to yield the acylated derivative of the compound of formula (IV).

Di-substituted carbamates may be prepared as described below in relation to the compounds of formula (I).

Compounds of formula (IV) wherein $R^4$ represents the residue of a sulphur nucleophile may readily be prepared by reaction of an ester of a halo derivative of clavulanic acid with a sulphur nucleophile as described in our German OLS No. 2708330. Other methods for preparing such sulphur compounds are also described in our above application.

Compounds of formula (I) in which $R^4$ is an acyloxy group may be prepared from compounds of formula (I) in which $R^4$ is hydroxyl by acylation as described above in relation to the compounds of formula (IV). In addition compounds of formula (I) in which $R^4$ is a disubstituted carbamate group may be prepared by reaction of a compound of formula (I) in which $R^4$ is hydroxyl with a carbamoyl halide of formula $R^9R^{10}NCOX$ (in which $R^9$ and $R^{10}$ are as defined above other than hydrogen and X is a halogen atom e.g. a chlorine atom) preferably in the presence of a weak base as hydrogen halide acceptor.

The carbamoyl halide may be prepared by reaction of a carbonyl dihalide such as phosgene with a secondary amine. Alternatively, a compound of formula (I) in which $R^4$ is hydroxyl may be reacted with a carbonyl dihalide followed by reaction with a secondary amine.

The esters of clavulanic acid may be prepared from the acid or a reactive derivative thereof by reaction with an alcohol, phenol or stannanol or a reactive derivative thereof to form the desired ester as described in our German OLS No. 2657081. Other esters of formula (IV) may be prepared in similar manner.

The preparation of the compounds of formula (IV) often results in the production of small amounts of the E isomer, i.e. where the $-CH_2R^4$ group is trans with respect to the ring oxygen atom, the major product being the Z isomer. Thus, the starting material of formula (IV) may be a mixture of E and Z isomers, but the shift of the double bond in the process of the invention renders this of no consequence.

The compounds of formula (IV) in their E-isomeric form may also be prepared directly from the E-isomer of clavulanic acid by methods analogous to those described above.

The compounds of formula (II) wherein $R^{17}$ and $R^4$ are as defined above may readily be prepared from corresponding compounds of formula (IV) by reaction at elevated temperature in the presence of a tertiary organic base such as, for example, an amine of formula $R^1R^2R^3N$, wherein $R^1$, $R^2$ and $R^3$ are as defined above, other than an aromatic heterocyclic amine, in a suitable inert solvent e.g. an ester such as ethyl acetate. Reaction will desirably be carried out at from 50° to 100° C., preferably under reflux.

As indicated above certain compounds of formula (I) are useful for the preparation of compounds of formula (III).

Such compounds of formula (I) are those in which $R^4$ is hydroxyl or a readily eliminatable substituent.

The compounds of formula (I) in which $R^4$ is a readily eliminatable substituent, such as a dichloroacetoxy group, can be converted into compounds of formula (III) by reaction with a tertiary organic base. The compounds of formula (I) in which $R^4$ is hydroxyl can be converted into compounds of formula (III) by reaction with reagents serving to replace the hydroxyl group by a readily eliminatable group which then undergoes elimination in the presence of a tertiary organic base. The tertiary organic base may be present during replacement of the hydroxyl group or may be added subsequently. The base may, for example, be a tertiary amine (including a heterocyclic aromatic amine).

Suitable amines will include amines bearing aliphatic, araliphatic or aromatic groups, e.g. alkyl groups having up to 8 carbon atoms, aralkyl groups having up to 6 carbon atoms in the alkyl portion, or an aryl group, such aryl and aralkyl groups desirably being monocyclic. Amines bearing cycloaliphatic e.g. $C_{3-7}$ cycloalkyl groups or amines wherein the nitrogen atom forms part of a five-, six- or seven-membered heterocyclic ring optionally containing a further heteroatom, e.g. N-alkyl piperidines or N-alkyl morpholines are also suitable. Suitable aromatic heterocyclic bases include pyridine bases e.g. collidine.

Preferred bases include trialkylamines preferably having 1–6 carbon atoms in each alkyl group, especially methyl, ethyl, propyl or butyl groups, and triethylamine is particularly suitable.

Reaction will generally be effected in a suitable inert solvent. Such solvents will preferably have some degree of polarity and include esters e.g. ethyl acetate, ethers e.g. tetrahydrofuran, ketones e.g. acetone, amides e.g. dimethylformamide or halogenated hydrocarbons e.g. 1,2-dichloroethane or chloroform.

Reaction will be effected at elevated temperature, desirably under reflux, a temperature of from 50° C. to 100° C. being preferred.

Thus, for example, a compound of formula (I) in which $R^4$ is hydroxyl may be reacted in the presence of the tertiary organic base, e.g. triethylamine, with a sulphonylating agent such as a mesyl or tosyl halide in the presence or absence of halide ions, or with other acylating reagents serving to introduce a readily eliminatable group or with a halogenating reagent such as thionyl chloride to produce a diene ester of formula (III).

The invention will now be further described in the following preparations and Examples which should not be construed as limiting the invention.

The following preparations illustrate the means whereby the starting materials for the preparation of the compounds of the invention may be obtained.

PREPARATION 1

Methyl(3R,5R,Z)-2-ethylideneclavam-3-carboxylate

A suspension of lithium (3R,5R,Z)-2-(2-hydroxyethylidene)clavam-3-carboxylate (4.0 g) in a mixture of brine (50 ml) and ethyl acetate (50 ml) was acidified with 2 N hydrochloric acid (15 ml) and shaken. The separated aqueous phase was further extracted with ethyl acetate and the combined organic solutions were dried, and filtered. The resulting ethyl acetate solution of free acid was hydrogenated at atmospheric pressure and ambient temperature over 5% palladium on carbon (6.0 g). Hydrogenation was terminated after 3 minutes when the initial rapid uptake of hydrogen (ca 630 ml) had ceased. The mixture was filtered through Kieselguhr and the organic solution was washed successively with water and brine and dried. The solution was filtered, concentrated by evaporation to ca. 50 ml, cooled to 0° and treated dropwise with an excess of ethereal diazomethane. Evaporation of the solvents afforded an oil which was chromatographed on a dry column of silica gel and eluted with ether-petroleum (b.p. 40°-60°) (1:2). Fractions were combined on the basis of t.l.c. examination and evaporated to afford a colourless oil which was redissolved in chloroform and evaporated to yield the title ester (1.42 g) which contained about 15% of the corresponding E-isomer, $[\alpha]_D +97.8°$ (c 0.8; DMSO), $\nu_{max}$ (CHBr$_3$) 1788 cm$^{-1}$ ($\beta$-lactam); $\tau$ (CDCl$_3$) values for Z-isomer include 4.35 (d, J 2 Hz, C—5H), 6.23 (s, methyl ester), 8.32 (dd, J 1 and 7 Hz, C=C—CH$_3$), $\tau$ (CDCl$_3$) values for E-isomer include 4.90 (m, C—5H).

PREPARATION 2

4-Nitrobenzyl (3R,5R,Z)-2-ethylideneclavam-3-carboxylate

A stirred solution of sodium (3R,5R,Z)-2-ethylideneclavam-3-carboxylate (3.0 g) in N,N-dimethylformamide (40 ml) was cooled in ice and treated with 4-nitrobenzylbromide (3.16 g). The resulting solution was stirred at room temperature for 2 hr. and was then partitioned between ethyl acetate and brine. The organic solution was washed successively with brine, water and brine and was then dried. Evaporation afforded an oil which crystallised on standing. Recrystallisation from ether-petroleum (b.p. 40°-60°) gave the title ester (2.67 g) which contained less than 2% E-isomer; m.p. 81.6°, $[\alpha]_D +73°$ (c 0.7 DMSO) $\lambda_{max}^{EtOH}$ 263 mm ($\epsilon$ 10,200), $\nu_{max}$ (CHBr$_3$) 1780 cm$^{-1}$ ($\beta$-lactam), $\tau$ (CDCl$_3$) values include 4.35 (d, J 2 Hz, C-5H), 8.36 (dd, J 1 and 7 Hz, C=C—CH$_3$).

PREPARATION 3

4-Nitrobenzyl (3R,5R,Z)-2-(2-benzoyloxyethylidene)clavam-3-carboxylate

A solution of 4-nitrobenzyl (3R,5R,Z)-2-(2-hydroxyethylidene)clavam-3-carboxylate (2.0 g) in ethyl acetate (40 ml) was cooled to 0°, stirred and treated with pyridine (3.22 ml) and benzoyl chloride (1.39 ml). The mixture was allowed to reach ambient temperature, stirred for 1 hour and then partitioned between ethyl acetate and 0.5 N hydrochloric acid. The organic phase was washed with 0.5 N aqueous sodium hydrogen carbonate and water. The solution was dried over sodium sulphate and evaporated to dryness in the pressure of chromatographic silica gel (7 g). The resulting powder was added to the top of a dry column of silica gel and eluted with mixtures of petroleum spirit (b.p. 40°-60°) and ether. Fractions were collected and combined on the basis of t.l.c. examination and evaporated to afford the title ester (2.267 g). $[\alpha]_D$ (c 0.43 DMSO) +18°, $\lambda_{max}$ (EtOH) 260 nm ($\epsilon$ 12, 360), $\nu_{max}$ (CHBr$_3$) 1798 cm$^{-1}$ ($\beta$-lactam), $\tau$ (CDCl$_3$) values include ca. 1.95 and ca. 2.5 (m, COPh), 4.21 (d, J 3 Hz, C—5H).

PREPARATION 4

4-Nitrobenzyl (3R,5R,Z)-2-(2-tert-butyldimethylsilyoxyethylidene)-clavam-3-carboxylate A solution of imidazole (1.67 g) in ethyl acetate (25 ml) was added to a stirred solution of 4-nitrobenzyl (3R,5R,Z)-2-(2-hydroxyethylidene)clavam-3-carboxylate (8.44 g) in ethyl acetate (125 ml) containing tert-butyldimethylsilyl chloride (3.69 g). After 30 minutes the mixture was filtered and the filtrate was evaporated to dryness and then fractionated on a column of silica gel. Appropriate fractions were combined and evaporated to give the title ester (6.5 g), $\nu_{max}$ (CHBr$_3$) 1798 ($\beta$-lactam), 1752 (ester), 1522 and 1348 cm$^{-1}$ (NO$_2$), $\tau$ (CDCl$_3$) 1.79 and 2.51 (doublets, J 9 Hz, aromatic protons), 4.33 (d, J 3 Hz, C—5H), 4.73 (s, benzylic protons), 4.90 (d, J 1 Hz, C—3H), 5.18 (dt, J 7 and 1 Hz, olefinic proton), 5.73 (d, J 7 Hz, C=C—CH$_2$), 6.49 and 6.96 (dd, J 17 and 3 Hz, and d, J 17 Hz, C-6 protons), 9.11 (s, Si(CH$_3$)$_2$—C(CH$_3$)$_3$), 9.91 (s, Si(CH$_3$)$_2$—C(CH$_3$)$_3$).

PREPARATION 5

4-Nitrobenzyl (3R,5R,Z)-2-(2-acetoxyethylidene)clavam-3-carboxylate

A stirred solution of 4-nitrobenzyl (3R,5R,Z)-2-(2-hydroxyethylidene)clavam-3-carboxylate (1.0 g) in ethyl acetate (25 ml) at 0° was treated with pyridine (1.61 ml) followed by acetyl chloride (0.43 ml). The mixture was stirred at ambient temperature for 3½ hours and then partitioned between ethyl acetate and 0.5 N hydrochloric acid. The organic phase was washed with saturated aqueous sodium hydrogen carbonate, water and brine and was then dried over sodium sulphate. Evaporation of the solvent gave an oil which crystallized on standing to yield the title ester (1.19 g), m.p. 62.5°-63.5°, $[\alpha]_D +42°$ (c 0.96; DMSO), $\lambda_{max}$ (EtOH) 264.5 nm ($\epsilon$ 11,000), $\nu_{max}$ (CHBr$_3$) 1792 ($\beta$-lactam), $\tau$ (CDCl$_3$) values include 4.27 (d, J 2.5 Hz, C—5H), 5.33 (d, J 7 Hz, —CH$_2$OCOCH$_3$), 7.95 (s, CH$_3$).

EXAMPLE 1

1-(4-Nitrobenzyloxycarbonyl)-1-(2-oxo-4-triethylammonioazetidin-1-yl)but-1-en-2-olate A solution of 4-nitrobenzyl (3R,5R,Z)-2-ethylideneclavam-3-carboxylate (1.0 g) and triethylamine (0.84 ml) in ethyl acetate (15 ml) was stood at ambient temperature for 24 hours. The resulting crystalline mass was broken up, collected, washed with ethyl acetate and with ether and was then dried in vacuo to afford the title salt (0.812 g), m.p. 110°–112°, $[\alpha]_D$ 0°±1° (c 1.0, $H_2O$), $\lambda_{max}$ (pH 6 buffer) 273.5 nm ($\epsilon$ 29,800), $\nu_{max}$ (Nujol) 1770 cm$^{-1}$ ($\beta$-lactam), $\tau$ (DMSO-$d_6$) values for ca. 1:1 mixture of isomers include 4.48+4.90[obscured] (m, azetidinyl C—4H), 7.2 to 7.7 (m, C$\underline{H}_2$CH$_3$), 8.82+8.90 (t, J8 Hz, N(CH$_2$C$\underline{H}_3$)$_3$), and 9.06+9.08 (t, J 8 Hz, CH$_2$C$\underline{H}_3$).

A portion of the product (0.2 g) was recrystallised from water (3 ml) to give material (0.066 g) with m.p. 116°–118° and spectral characteristics similar to those above.

EXAMPLE 2

1-Benzyloxycarbonyl-1-(2-oxo-4-triethylammonioazetidin-1-yl)but-1-en-2-olate

A solution of benzyl (3R,5R,Z)-2-ethylideneclavam-3-carboxylate (0.547 g) and triethylamine (0.55 ml) in N,N-dimethylformamide (1 ml) was stood at ambient temperature for 18 hours and then diluted with ether. The resulting oil was triturated with ethyl acetate to give a solid which was collected and dried in vacuo to afford the title salt (0.358 g), m.p. 107°, $\lambda_{max}$ (pH 6 buffer) 272.5 nm ($\epsilon$ 19,100), $\nu_{max}$ (Nujol) 1762 cm$^{-1}$ ($\beta$-lactam) $\tau$ (D$_2$O) values for mixture of isomers include 4.42+4.78 (m, azetidinyl C—4H), 7.0 to 7.4 (m, C$\underline{H}_2$CH$_3$), 8.59+8.76 (t, J 7 Hz, CH$_2$C$\underline{H}_3$) and 8.88 (t, J 7 Hz, N(CH$_2$C$\underline{H}_3$)$_3$).

EXAMPLE 3

1-Methoxycarbonyl-1-(2-oxo-4-triethylammonioazetidin-1-yl)but-1-en-2-olate

A solution of methyl (3R,5R,Z)-2-ethylideneclavam-3-carboxylate (0.5 g) and triethylamine (0.7 ml) in N,N-dimethylformamide (0.5 ml) was stood at ambient temperature for 4 hours and then diluted with ethyl acetate. The resulting crystalline precipitate was collected, washed with ethyl acetate and with ether, and then dried in vacuo to yield the title salt (0.398 g), m.p. 109°–109.5°, $\lambda_{max}$ (pH 6 buffer) 270 nm ($\epsilon$ 20,500), $\lambda_{max}$ (Nujol) 1767 cm$^{-1}$ ($\beta$-lactam) $\tau$ (DMSO-$d_6$) values for ca 1:1 mixture of isomers include 4.48+4.80 (m, azetidinyl C—4H), 6.30 (s, CO$_2$CH$_3$), 7.1 to 7.7 (m, C$\underline{H}_2$CH$_3$), 8.78 (t, J 7 Hz, N(CH$_2$C$\underline{H}_3$)$_3$), and 9.06+9.08 (t, J 7 Hz, CH$_2$C$\underline{H}_3$).

EXAMPLE 4

4-Benzoyloxy-1-(4-nitrobenzyloxycarbonyl)-1-(2-oxo-4-triethylammonioazetidin-1-yl)but-1-en-2-olate A solution of 4-nitrobenzyl (3R,5R,Z)-2-(2-benzoyloxyethylidene)clavam-3-carboxylate (0.657 g) and triethylamine (3.03 g) in ethyl acetate (15 ml) was stood at ambient temperature for 5 hours. The supernatant was decanted from deposited solid which was then washed with ethyl acetate and with ether. The solid was dried in vacuo to give the title salt (0.502 g) m.p. 133°–4°. $\nu_{max}$ (Nujol) 1784 ($\beta$-lactam), 1712 cm$^{-1}$.(—O-COPh), $\tau$ (DMSO-$d_6$) values for mixture of isomers include 4.44+4.80 (m, azetidinyl C—4H), 5.50 (CH$_2$O-COPh), ca. 6.64 (azetidinyl C-3 protons and N(C$\underline{H}_2$CH$_3$)$_3$), 8.84+8.90 (t, N(CH$_2$C$\underline{H}_3$)$_3$).

EXAMPLE 5

4-Hydroxy-1-methoxycarbonyl-1-(2-oxo-4-triethylammonioazetidin-1-yl)but-1-en-2-olate A solution of methyl (3R,5R,Z)-2-(2-hydroxyethylidene) clavam-3-carboxylate (2.0 g) and triethylamine (2.8 ml) in ethyl acetate (50 ml) was stood at ambient temperature for 1½ hours, diluted with ethyl acetate (25 ml) and stood for a further 18 hours. The resulting crystalline solid was collected, washed with ethyl acetate and with ether, and was then dried in vacuo to yield the title salt (1.84 g), $[\alpha]_D$ 0°±1° (c 1.0, DMSO), $\lambda_{max}$ (pH 6 buffer) 270.5 nm ($\epsilon$ 16,800), $\nu_{max}$ (Nujol) 1760 cm$^{-1}$ ($\beta$-lactam) $\tau$ (DMSO-$d_6$ values for ca. 1:1 mixture of isomers include 4.48+4.80 (m, azetidinyl C-4 H), 6.50 (s, CO$_2$CH$_3$), and 8.78 (t, J 7 Hz, N(CH$_2$C$\underline{H}_3$)$_3$).

EXAMPLE 6

4-Hydroxy-1-(4-nitrobenzyloxycarbonyl)-1-(2-oxo-4-triethylammonioazetidin-1-yl)but-1-en-2-olate A solution of 4-nitrobenzyl (3R,5R,Z)-2-(2-hydroxyethylidene)clavam-3-carboxylate (0.334 g) and triethylamine (0.27 ml) in ethyl acetate (10 ml) was stirred at ambient temperature for 5 hours during which time an oil was deposited. The mixture was stood for a further 18 hours and the supernatant then decanted from the oil. Trituration of the oil with ethyl acetate gave a solid which was collected, washed with ether and dried in vacuo to yield the title salt (0.261 g), $[\alpha]_D$ 0°±1° (c 1.0, H$_2$O), $\lambda_{max}$ (pH 6 buffer) 274.5 nm ($\epsilon$ 25,000), $\nu_{max}$ (Nujol) 1764 cm$^{-1}$ ($\beta$-lactam), $\tau$ (DMSO-$d_6$) values for ca. 1:1 mixture of isomers include 4.50+4.65 (m, azetidinyl C-4 H), and 8.81+8.88 (t, J 7 Hz, N(CH$_2$C$\underline{H}_3$)$_3$).

EXAMPLE 7

1-(4-Nitrobenzyloxycarbonyl)-1-(2-oxo-4-trimethylammonioazetidin-1-yl)but-1-en-2-olate A solution of 4-nitrobenzyl (3R,5R,Z)-2-ethylideneclavam-3-carboxylate (0.5 g) in ethyl acetate (2.5 ml) was treated with a solution of trimethylamine in ethyl acetate (1.3 M, 2.5 ml). An oil soon began to separate and the mixture was diluted with ethyl acetate and left at ambient temperature for 24 hours. The resulting crystalline solid was collected, washed with ethyl acetate and with ether, and then dried in vacuo to give the title salt (0.39 g), m.p. 131° (dec.), $\lambda_{max}$ (H$_2$O) 273 nm ($\epsilon$ 27,400), $\nu_{max}$ $\tau$ (DMSO-$d_6$) values for ca. 1:1 mixture of isomers include 4.64+4.96 (m, azetidinyl C-4H), 6.78 (s, N(CH$_3$)$_3$), and 9.04 (t, J 7 Hz, CH$_2$C$\underline{H}_3$).

EXAMPLE 8

4-Nitrobenzyl-2-ethylclav-2-em-3-carboxylate

A suspension of 1-(4-nitrobenzyloxycarbonyl)-1-(2-oxo-4-triethylammonioazetidin-1-yl)but-1-en-olate (4.5 g) in ethyl acetate (250 ml) was heated rapidly and refluxed for 2 minutes to dissolve. The cooled solution was concentrated to ca. 20 ml, diluted with ether and allowed to crystallise. The resulting crystalline mass was broken up, collected, washed with ether and dried in vacuo to afford the title ester (2.65 g), m.p. 116°–118°, $[\alpha]_D$ 0°±1° (c 1.0, DMSO), $\nu_{max}$ (Nujol) 1806 cm$^{-1}$ ($\beta$-lactam), $\tau$ (DMSO-$d_6$) values include 3.96 (m, C-5H), 7.1 to 7.5 (m, C$\underline{\text{H}}_2$CH$_3$) and 8.90 (t, J 7 Hz, CH$_2$C$\underline{\text{H}}_3$).

EXAMPLE 9

2-Ethylclav-2-em-3-carboxylic acid

A solution of 4-nitrobenzyl 2-ethylclav-2-em-3-carboxylate (0.10 g) in ethyl acetate (7 ml) was hydrogenated for ca. 1 minute at atmospheric pressure and ambient temperature over 10% palladium on carbon (0.10 g). The catalyst was removed by filtration through Kieselguhr and washed with ethyl acetate (10 ml). The combined organic solutions were extracted with pH 7 buffer ($2 \times 10$ ml). The aqueous extract was washed with ether and made up to a volume of 100 ml. with pH 7 buffer to afford a solution of the title acid. A portion of the above freshly prepared solution diluted 1 to 10 with pH 7 buffer showed $\lambda_{max}$ 263 nm with an absorbance of 1.49 in a 1 cm cell.

EXAMPLE 10

1-(4-Nitrobenzyloxycarbonyl)-1-(2-oxo-4-triethylammonioazetidin-1-yl)but-1-en-2-olate A stirred suspension of 4-nitrobenzyl 2-ethylclav-2-em-3-carboxylate (0.32 g) in ethyl acetate (3 ml) was treated with triethylamine (0.27 ml). The mixture was stirred for 18 hours and the precipitate collected, washed with ethyl acetate and with ether, and then dried in vacuo to give the title salt (0.363 g). The physical and spectral characteristics of the product were similar to those described in Example 1.

EXAMPLE 11

1-(4-Nitrobenzyloxycarbonyl)-1-(2-oxo-4-pyridiniumazetidin-1-yl)but-1-en-2-olate A solution of 4-nitrobenzyl 2-ethylclav-2-em-3-carboxylate (0.69 g) and pyridine (0.37 ml) in ethyl acetate (9 ml) was stood at ambient temperature for 3 hours and deposited an oil. The supernatant was removed and the oil triturated with ethyl acetate to give a solid. The solid was collected, washed with ethyl acetate and with ether, and was then dried in vacuo to afford the title salt (0.44 g), $\lambda_{max}$ (pH 6 buffer) 272 nm ($\epsilon$ 26,100), $\nu_{max}$ (Nujol) 1781 ($\beta$-lactam), $\tau$ (DMSO-d$_6$) values include 3.53 (m, azetidinyl C-4H), 6.37 and 6.69 (dd, J 17 and 4 Hz, and d, J 17 Hz, azetidinyl C-3 protons) and 9.09 (t, J 7 Hz, CH$_2$C$\underline{\text{H}}_3$).

EXAMPLE 12

4-Nitrobenzyl 2-ethylclav-2-em-3-carboxylate

A suspension of 1-(4-nitrobenzyloxycarbonyl)-1-(2-oxo-4-pyridiniumazetidin-1-yl)but-1-en-2-olate (0.05 g) in ethyl acetate (10 ml) was heated under reflux for 5 minutes to dissolve. The solution was evaporated to give an oil which crystallised on trituration with ether to afford the title ester (0.035 g). The spectral characteristics of the product were similar to those described in Example 8.

EXAMPLE 13

1-(4-Nitrobenzyloxycarbonyl)-1-(2-oxo-4-triethylammonioazetidin-1-yl)but-1-en-2-ol-4-toluenesulphonate 4-Toluenesulphonic acid monohydrate (0.095 g) was added to a solution of 1-(4-nitrobenzyloxycarbonyl)-1-(2-oxo-4-triethylammonioazetidin-1-yl)but-1-en-2-olate (0.205 g) in dimethylformamide (1 ml). After 10 minutes the solution was diluted with ether and the supernatant was decanted from the deposited oil. Trituration of the oil with ether gave a solid which was collected, washed with ether, and dried in vacuo to yield the title salt (0.150 g) $\lambda_{max}$ (pH 6 buffer) 273.5 nm ($\epsilon$ 27,300), $\nu_{max}$ (Nujol) 2640 (OH), 1790 ($\beta$-lactam), 1032 cm$^{-1}$ (SO$_3^-$), $\tau$, (DMSO-d$_6$) values include 2.50 and 2.90 (doublets, J 9 Hz, $^-$O$_3$SC$_6$H$_4$CH$_3$), 6.2 to 6.9 (m, C-3 protons, N(C$\underline{\text{H}}_2$CH$_3$)$_3$, and C$\underline{\text{H}}_2$CH$_3$), 7.50 (s, $^-$O$_3$SC$_6$H$_4$C$\underline{\text{H}}_3$), 8.82 and 8.88 (multiplets, N(CH$_2$C$\underline{\text{H}}_3$)$_3$ and CH$_2$C$\underline{\text{H}}_3$).

EXAMPLE 14

4-Nitrobenzyl 2-ethylclav-2-em-3-carboxylate

A suspension of 1-(4-nitrobenzyloxycarbonyl)-1-(2-oxo-4-triethylammonioazetidin-1-yl)but-1-en-2-ol 4-toluenesulphonate (0.041 g) in ethyl acetate (30 ml) was heated gently under reflux for 5 minutes. The resulting mixture was cooled to 25° and then filtered. The filtrate was evaporated to afford the title ester (0.032 g), whose spectral characteristics were similar to those as described in Example 8.

EXAMPLE 15

4-N,N-Dimethylthiocarbamoylthio-1-(4-nitrobenzyloxycarbonyl)-1-(2-oxo-4-triethylammonioazetidin-1-yl)but-1-en-2-olate A solution of 4-nitrobenzyl (3R,5R,Z)-2-(2-N,N-dimethylthiocarbamoylthioethylidene)clavam-3-carboxylate (0.044 g) and triethylamine (0.03 ml) in ethyl acetate (1 ml) was stood at ambient temperature for 1 hour and then diluted with ether. The resulting oil was triturated with ether to give a solid which was collected and dried in vacuo to afford the title salt (0.04 g), $\nu_{max}$ (Nujol) 1772 cm$^{-1}$ ($\beta$-lactam), $\tau$ (DMSO-d$_6$) values for ca. 1:1 mixture of isomers include 4.50+4.90 [obscured] (m, azetidinyl C-4H), 8.82+8.90 (t, J 7 Hz, N(CH$_2$C$\underline{\text{H}}_3$)$_3$).

EXAMPLE 16

4-Acetylthio-1-(4-nitrobenzyloxycarbonyl)-1-(2-oxo-4-triethylammonioazetidin-1-yl)but-1-en-2-olate A solution of 4-nitrobenyl (3R,5R,Z)-2-(2-acetylthioethylidene)clavam-3-carboxylate (0.078 g) and triethylamine (0.06 ml) in ethyl acetate (1 ml) was stood at ambient temperature for 1 hour and then diluted with ether. The resulting oil was triturated with ether to give a solid which was collected and dried in vacuo to afford the title salt (0.035 g), $\nu_{max}$ (Nujol) 1770 ($\beta$-lactam), 1680 cm$^{-1}$ (SCOR), $\tau$ (DMSO-d$_6$) values for ca. 1:1 mixture of isomers include 4.50+4.90 [obscured] (m, azetidinyl C-4H), 6.9 to 7.3 (m, —C$\underline{\text{H}}_2$CH$_2$S—), 8.80+8.88 (t, J 7 Hz, N(CH$_2$C$\underline{\text{H}}_3$)$_3$).

EXAMPLE 17

4-Benzoylthio-1-(4-nitrobenzyloxycarbonyl)-1-(2-oxo-4-triethylammonioazetidin-1-yl)but-1-en-2-olate A solution of 4-nitrobenzyl (3R,5R,Z)-2-(2-benzoylthioethylidene)clavam-3-carboxylate (0.045 g) and triethylamine (0.03 ml) in ethyl acetate (1 ml) was stood at ambient temperature for 1 hour. The resulting crystalline solid was collected and dried in vacuo to yield the title salt (0.039 g), $\nu_{max}$ (CHBr$_3$) 1782 ($\beta$-lactam), 1626 cm$^{-1}$ (SCOAr), $\tau$ (DMSO-d$_6$) values for mixture of isomers include 2.13+2.45 (complex multiplets COPh), 4.48+4.90 [obscured] (m, azetidinyl C-4H), 8.82+8.90 (t, J 7 Hz, N(CH$_2$C$\underline{\text{H}}_3$)$_3$).

EXAMPLE 18

1-(4-Nitrobenzyloxycarbonyl)-1-(2-oxo-4-triethylammonioazetidin-1-yl)-4-phenylthiobut-1-en-2-olate A solution of 4-nitrobenzyl (3R,5R,Z)-2-(2-phenylthioethylidene)clavam-3-carboxylate (0.548 g) and triethylamine (0.35 ml) in ethyl acetate (2 ml) was stood at ambient temperature for 1 hour and the supernatant was then decanted from the deposited oil. Trituration of the oil with ethyl acetate gave a solid which was collected, washed with ether, and dried in vacuo to yield the title salt (0.272 g), $[\alpha]_D$ 0°±1° (c 1.0, $H_2O$), $\nu_{max}$ (Nujol) 1768 cm$^{-1}$ ($\beta$-lactam), $\tau$ (DMSO-$d_6$) values for mixture of isomers include 2.5 to 2.9 (m,SPh), 4.48+4.90 [obscured] (m, azetidinyl C-4H), 8.82+8.89 (t, J 7 Hz, N($CH_2C\underline{H}_3$)$_3$).

EXAMPLE 19

1-(4-Nitrobenzyloxycarbonyl)-1-(2-oxo-4-triethylammonioazetidin-1-yl)-4-phenylsulphonylbut-1-en-2-olate A solution of 4-nitrobenzyl (3R,5R,Z) 2-(2-phenylsulphonylethylidene)clavam-3-carboxylate (0.046 g) and triethylamine (0.02 g) in ethyl acetate (1 ml) was stood at ambient temperature for 1 hour. The mixture was diluted with ether and the precipitated solid was collected and dried in vacuo to afford the title salt (0.018 g), $\nu_{max}$ (Nujol) 1778 cm$^{-1}$ ($\beta$-lactam), $\tau$ (DMSO-$d_6$) values for mixture of isomers include 2.0 to 2.4 (m, $SO_2$Ph), 4.56+4.64 (m, azetidinyl C-4H), 8.80+8.88 (t, J 7 Hz, N($CH_2C\underline{H}_3$)$_3$).

EXAMPLE 20

4-Mercapto-1-(4-nitrobenzyloxycarbonyl)-1-(2-oxo-4-triethylammonioazetidin-1-yl)but-1-en-2-olate Triethylamine (0.085 ml) was added to a solution of 4-nitrobenzyl (3R,5R,Z)-2-(2-mercaptoethylidene)-clavam-3-carboxylate carboxylate (0.105 g) in ethyl acetate (3 ml) containing N,N-dimethylformamide (0.5 ml). After 1 hour the reaction mixture was diluted with petroleum ether (40°–60°) (50 ml) and the precipitated solid was collected and dried in vacuo to give the title salt (0.06 g), $\nu_{max}$ (Nujol) 1774 cm$^{-1}$ ($\beta$-lactam), $\tau$ (DMSO-$d_6$) values for mixture of isomers include 4.52+4.66 (m, azetidinyl C-4H), 8.81+8.89 (m, N($CH_2C\underline{H}_3$)$_3$).

EXAMPLE 21

4-Methylthio-1-(4-nitrobenzyloxycarbonyl)-1-(2-oxo-4-triethylammonioazetidin-1-yl)but-1-en-2-olate A solution of 4-nitrobenzyl (3R,5R,Z) 2-(2-methylthioethylidene)clavam-3-carboxylate (2.263 g) and triethylamine (1.73 ml) in ethyl acetate (20 ml) was stood at 23° for 1.5 hours. The precipitated oil was triturated with ether to afford a solid which was collected and dried in vacuo to give the title salt (1.97 g), m.p. 91.0° (Mettler), $\nu_{max}$ (Nujol) 1772 cm$^{-1}$ ($\beta$-lactam), $\tau$ (DMSO-$d_6$) values for mixture of isomers include 4.46+4.61 (m, azetidinyl C-4H), 7.95 (s, SMe), 8.79+8.86 (t, J 7 Hz, N($CH_2C\underline{H}_3$)$_3$).

EXAMPLE 22

1-(4-Nitrobenzyloxycarbonyl)-1-(2-oxo-4-triethylammonioazetidin-1-yl)-4-(tetrahydropyran-2-yloxy)but-1-en-2-olate A solution of 4-nitrobenzyl (3R,5R,Z)-2-{2[(2RS)-tetrahydropyran-2-yloxy]ethylidene}clavam-3-carboxylate (5.73 g) and triethylamine (2.76 g) in ethyl acetate (30 ml) was stood at ambient temperature for 16 hours. The resulting oil was triturated with ether to give a solid which was collected and dried in vacuo to afford the title salt (3.29 g), $\lambda_{max}$ (pH 6 buffer) 274 nm ($\epsilon$ 23,400), $\nu_{max}$ (Nujol) 1774 cm$^{-1}$ ($\beta$-lactam), $\tau$ (DMSO-$d_6$) values for ca. 1:1 mixture of isomers include 4.52+4.62 (m, azetidinyl C-4H), 5.48 (m, tetrahydropyranyl C-2H), 8.1 to 8.7 (m, tetrahydropyranyl C-3, C-4, and C-5 protons), 8.82 and 8.89 (t, J 7 Hz, N($CH_2C\underline{H}_3$)$_3$).

EXAMPLE 23

4-Methoxy-1-(4-nitrobenzyloxycarbonyl)-1-(2-oxo-4-triethylammonioazetidin-1-yl)but-1-en-2-olate A solution of 4-nitrobenzyl (3R,5R,Z)-2-(2-methoxyethylidene)clavam-3-carboxylate (10.45 g) and triethylamine (8.36 ml) in ethyl acetate (50 ml) was stood at ambient temperature for 23 hours and then diluted with ether (150 ml). The resulting oil was triturated with ether to give a solid which was collected and dried in vacuo to afford the title salt (13.27 g), $\lambda_{max}$ (pH 6 buffer) 274 nm ($\epsilon$ 26,600), $\nu_{max}$ (Nujol) 1770 cm$^{-1}$ ($\beta$-lactam), $\tau$ (DMSO-$d_6$) values include for mixture of isomers 4.47+4.63 (m, azetidinyl C-4H), 6.78 (s, $OCH_3$), 8.79+8.86 (t, J 7 Hz, N($CH_2C\underline{H}_3$)$_3$).

EXAMPLE 24

4-(1-Ethoxyethoxy)-1-(4-nitrobenzyloxycarbonyl)-1-(2-oxo-4-triethylammonioazetidin-1-yl)but-1-en-2-olate A solution of 4-nitrobenzyl (3R,5R,Z)-2-{2-[(1RS)-1-ethoxyethoxy]ethylidene}clavam-3-carboxylate (9.92 g) and triethylamine (6.81 ml) in ethyl acetate (20 ml) was stood at ambient temperature for 18 hours. The resulting solid was collected and washed with ether, and then dried in vacuo to afford the title salt (8.66 g), $\lambda_{max}$ (pH 6 buffer) 273.5 nm ($\epsilon$ 27,600), $\nu_{max}$ (Nujol) 1758 cm$^{-1}$ ($\beta$-lactam), $\tau$ (DMSO-$d_6$) values include for mixture of isomers 4.52+4.86 (m, azetidinyl C-4H), 5.40 (q, J 5 Hz, O—C$\underline{H}$($CH_3$)OEt), 8.82+8.90 (t, J 7 Hz, N($CH_2C\underline{H}_3$)$_3$), 8.90 [partially obscured] (m, OCH(C$\underline{H}_3$)OEt).

EXAMPLE 25

4-Nitrobenzyl 2-vinylclav-2-em-3-carboxylate

A solution of 4-hydroxy-1-(4-nitrobenzyloxycarbonyl)-1-(2-oxo-4-triethylammonioazetidin-1-yl)but-1-en-2-olate (0.435 g) in chloroform (25 ml ethanol freed) was heated under reflux for 12 minutes. T.l.c. examination at this time indicated complete conversion to 4-nitrobenzyl 2-(2-hydroxyethyl)clav-2-em-3-carboxylate. The solution was treated with triethylamine (0.101 g) followed by mesyl chloride (0.1 ml) and reflux continued for a further 5 minutes. The cooled solution was diluted with petroleum spirit (ca. 225 ml) and some precipitated solid removed by filtration. The filtrate was washed with brine, dried over sodium sulphate and concentrated to afford a crystalline solid. The solid was collected, washed with petroleum spirit and dried in vacuo to give the title ester (0.112 g), $[\alpha]_D$ 0°±1° (c 1.0, DMSO). $\nu_{max}$ (CHBr$_3$) 1810 cm$^{-1}$ ($\beta$-lactam), $\tau$ (CDCl$_3$) values include 2.94 (dd, J10 and 17 Hz, —C$\underline{H}$=$CH_2$), 4.01 (dd, J2 and 3 Hz, C-5H), 4.03 (dd, J2 and 17 Hz, olefinic proton), 4.32 (dd, J2 and 10 Hz, olefinic proton).

EXAMPLE 26

4-Nitrobenzyl 2-vinylclav-2-em-3-carboxylate

To a suspension of 4-hydroxy-1-(4-nitrobenzyloxycarbonyl)-1-(2-oxo-4-triethylammonioazetidin-1-yl)but-1-en-2-olate (0.217 g) in alumina dried chloroform (30 ml) was added triethylamine (0.050 g) followed by methanesulphonyl chloride (0.068 g). The mixture was heated gently under reflux for 17 minutes and then allowed to cool to 25°. The reaction mixture was poured into petroleum ether (40°–60°) (200 ml) at 0° and the resulting suspension was filtered. The filtrate was evaporated to an oil which solidified on standing to afford the title ester (0.038 g). Spectral characteristics of the product were similar to those described in Example 25.

EXAMPLE 27

1-(4-Nitrobenzyloxycarbonyl)-1-(2-oxo-4-N,N,N-benzyldimethylammonioazetidin-1-yl)but-1-en-2-olate A solution of 4-nitrobenzyl (3R,5R,Z)-2-ethylideneclavam-3-carboxylate (320 mg) and N,N-dimethylbenzylamine (0.29 ml) in ethyl acetate (10 ml) was stood at ambient temperature for 18 hours and deposited an oil. Trituration of the oil gave a solid which was collected, washed and dried to yield the title salt (180 mg) $\lambda_{max}$ (pH 6 buffer) 274 nm ($\epsilon$ 31,700), $\nu_{max}$ (Nujol) 1778 cm$^{-1}$ ($\beta$-lactam), $\tau$ (DMSO-d$_6$) values for mixture of isomers include 4.62 (m, azetidinyl C—4H), 2.46 (s, Ph).

EXAMPLE 28

1-(4-Nitrobenzyloxycarbonyl)-1-(2-oxo-4-N-methylpiperidinioazetidin-1-yl)but-1-en-2-olate A solution of 4-nitrobenzyl (3R,5R,Z)-2-ethylideneclavam-3-carboxylate (320 mg) and N-methylpiperidine (0.245 ml) in ethyl acetate (10 ml) was stood at ambient temperature for 18 hours. The resulting solid was collected, washed and dried to give the title salt (290 mg), $\lambda_{max}$ (pH 6 buffer) 273.5 nm ($\epsilon$ 27,300), $\nu_{max}$ (Nujol) 1780 cm$^{-1}$ ($\beta$-lactam), $\tau$ (DMSO-d$_6$) values for mixture of isomers include 4.60 (m, azetidinyl C—4H), 6.75 and 6.95 (singlets, N—C$\underline{H}_3$).

EXAMPLE 29

1-(4-Nitrobenzyloxycarbonyl)-1-(2-oxo-4-pyridiniumazetidin-1-yl)-but-1-en-2-olate A solution of 4-nitrobenzyl (3R,5R,Z)-2-ethylideneclavam-3-carboxylate (0.316 g) in dry pyridine (2 ml) containing one drop of dry triethylamine was stood at room temperature for 18 hours. The resulting solution was diluted with ethyl acetate (3 ml) followed by ether (30 ml) and the deposited solid was collected, washed with ether, and was then dried in vacuo to afford the title salt (0.28 g) whose spectral characteristics resembled those as given in Example 11.

EXAMPLE 30

1-(4-Nitrobenzyloxycarbonyl)-1-(2-oxo-4-triethylammonioazetidin-1-yl)but-1-en-2-ol chloride A mixture of 1-(4-nitrobenzyloxycarbonyl)-1-(2-oxo-4-triethylammonioazetidin-1-yl)but-1-en-2-olate (210 mg) in water (10 ml) and 0.1 N hydrochloric acid (5 ml) was lyophilised and the residue triturated with ether to afford the title salt (220 mg), $\nu_{max}$ (Nujol) 1790 cm$^{-1}$ ($\beta$-lactam), $\tau$ (DMSO-d$_6$) values for mixture of isomers include 4.50 (m, azetidinyl C—4H), 6.3–6.8 (m, NC$\underline{H}_2$), 6.7–7.3 (m,

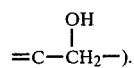

EXAMPLE 31

1-(4-Nitrobenzyloxycarbonyl)-1-(2-oxo-4-triethylammonioazetidin-1-yl)but-1-en-2-ol nitrate A mixture of 1-(4-nitrobenzyloxycarbonyl)-1-(2-oxo-4-triethylammonioazetidin-1-yl)but-1-en-2-olate (210 mg) in water (10 ml) and 1.0 N nitric acid (0.5 ml) was lyophilised and the residue triturated with ether to give the title salt (240 mg), $\nu_{max}$ (CHBr$_3$) 1794 cm$^{-1}$ ($\beta$-lactam), $\tau$ (DMSO-d$_6$) values for mixture of isomers include 4.50 l (m, azetidinyl C—4H), 6.7–7.4 (m,

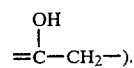

EXAMPLE 32

1-(4-Nitrobenzyloxycarbonyl)-1-(2-oxo-4-triethylammonioazetidin-1-yl)but-1-en-2-ol citrate A solution of 1-(4-nitrobenzyloxycarbonyl)-1-(2-oxo-4-triethylammonioazetidin-1-yl)but-1-en-2-olate (180 mg) and citric acid (90 mg) in water (10 ml) was lyophilised and the residue triturated with ether to yield the title salt (260 mg), $\nu_{max}$ (Nujol) 1784 ($\beta$-lactam), 1720 and 2650 (CO$_2$H) and 1580 cm$^{-1}$ (CO$_2$—), $\tau$ (DMSO-d$_6$) values for mixture of isomers include 4.50 (m, azetidinyl C—4H), 7.32 (citrate CH$_2$).

EXAMPLE 33

4-Acetoxy-1-(4-nitrobenzyloxycarbonyl)-1-(2-oxo-4-triethylammonioazetidin-1-yl)but-1-en-2-olate A solution of 4-nitrobenzyl (3R,5R,Z)-2-(2-acetoxyethylidene)clavam-3-carboxylate (375 mg) and triethylamine (0.27 ml) in ethyl acetate (15 ml) was stood at ambient temperature for 30 minutes and then diluted with ether until cloudiness was produced. The mixture was stood for a further 2 hours and the resulting precipitate collected, washed and dried to yield the title salt (260 mg), $\nu_{max}$ (Nujol) 1760 ($\beta$-lactam), 1720 cm$^{-1}$ (OAc), $\tau$ (DMSO-d$_6$) values for mixture of isomers include 4.54 (m, azetidinyl C—4H), 5.83 (t, J 7 Hz, C$\underline{H}_2$OAc), 8.10 (s, OCOCH$_3$).

EXAMPLE 34

4-N-Methylcarbamoyloxy-1-(4-nitrobenzyloxycarbonyl)-1-(2-oxo-4-triethylammonioazetidin-1-yl)but-1-en-2-olate A stirred solution of 4-hydroxy-1-(4-nitrobenzyloxycarbonyl)-1-(2-oxo-4-triethylammonioazetidin-1-yl)but-1-en-2-olate (400 mg) in dimethylformamide (10 ml) was treated with methyl isocyanate (0.06 ml). Further portions of methyl isocyanate (0.1 ml) were added after 30 mins and after a further 3 hours. The mixture was stirred for an hour after the final addition and was then poured into ether. The deposited gum was triturated with fresh ether to give the title salt as a solid (256 mg), $\lambda_{max}$ (pH 6 buffer) 274.5 nm ($\epsilon$ 26,250), $\nu_{max}$ (Nujol) 3320 (NH), 1770 ($\beta$-lactam), 1706 and 1512 cm$^{-1}$ (OCONH), τ (DMSO-d$_6$) values for mixture of isomers include 3.24 (m, OCONH), 4.50 (m, azetidinyl C—4H), 7.44 and 7.48 (OCONHC$\underline{H}_3$).

EXAMPLE 35

4-tert-Butyldimethylsilyloxy-1-(4-nitrobenzyloxycarbonyl)-1-(2-oxo-4-triethylammonioazetidin-1-yl)but-1-en-2-olate A solution of 4-nitrobenzyl (3R,5R,Z)-2-tert-butyldimethylsilyloxyethylidene)clavam-3-carboxylate (1.346 g) in ethyl acetate (4 ml) containing triethylamine (0.61 g) was stood at room temperature for 18 hours. The resulting solid was collected and dried in vacuo to afford the title salt (1.10 g), m.p. 109.0° (Mettler), ν$_{max}$ (Nujol) 1764 cm$^{-1}$ (β-lactam), τ (DMSO-d$_6$) values for mixture of isomers include 4.56 (m, azetidinyl C—4H), 8.85+8.93 (t, J 7 Hz, N(CH$_2$C$\underline{H}_3$)$_3$), 9.16 (s, OSi—(CH$_3$)$_2$—C(C$\underline{H}_3$)$_3$), 10.0 (s, OSi—(CH$_3$)$_2$—C(CH$_3$)$_3$).

EXAMPLE 36

4-Acetoxy-1-(4-nitrobenzyloxycarbonyl)-1-(2-oxo-4-triethylammonioazetidin-1-yl)but-1-en-2-olate A stirred solution of 4-hydroxy-1-(4-nitrobenzyloxycarbonyl)-1-(2-oxo-4-triethylammonioazetidin-1-yl)but-1-en-2-olate (400 mg) in dimethylformamide (20 ml) at 20° was treated with triethylamine (0.136 ml) followed by acetyl chloride (0.72 ml). After 10 minutes the reaction mixture was poured into stirred ether (ca 400 ml) and diluted with petroleum spirit (ca 100 ml, b.p. 40°–60°). The deposited gum was triturated to afford a solid which was collected, washed with ether and dried. The product (483 mg) was washed with water (ca 5 ml) and the insoluble residue was collected and dried to yield the title salt (102 mg), ν$_{max}$ (pH 6 buffer) 273 nm (ε 22,700), ν$_{max}$ (Nujol) 1768 (β-lactam) and 1720 cm$^{-1}$ (OAc), τ (DMSO-d$_6$) values resemble those described in Example 33.

We claim:

1. A compound of the formula (I)

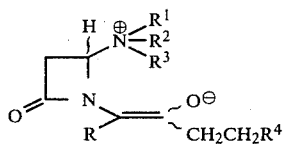

(I)

or a salt thereof with a carboxylic, sulphonic or mineral acid, wherein R is a group of formula —COOR$^{16}$ and R$^{16}$ is selected from the group consisting of C$_{1-8}$ alkyl and C$_{2-8}$ alkenyl, optionally substituted by methoxy, cyano, alkanoyloxy, p-bromobenzoyl or alkoxycarbonyl; benzyl; diphenylmethyl; triphenylmethyl; benzyl substituted on the ring by nitro, sulphonyl, cyano, alkyl or alkoxy, said substituted benzyl having up to 20 carbon atoms; a phenyl group optionally substituted by nitro, alkyl or alkoxy, said substituted phenyl group containing up to 12 carbon atoms; a cycloalkyl group containing up to 12 carbon atoms; a tetrahydropyranyl group; a phthalidyl group; and a stannyl group having up to 24 carbon atoms carrying three substituents selected from the group consisting of alkyl, alkenyl, phenyl, benzyl, cycloalkyl and alkoxy; R$^1$, R$^2$ and R$^3$, which may be the same or different, represent an alkyl group having up to 8 carbon atoms, a benzyl group or a C$_{3-7}$ cycloalkyl group, or two of R$^1$, R$^2$ and R$^3$ form, together with the nitrogen atom to which they are attached, a piperidino, morpholino or thiamorpholino group or R$^1$, R$^2$ and R$^3$ together may form part of a pyridinium, collidinium or quinuclidinium group; and R$^4$ represents (i) a hydrogen atom; (ii) a hydroxyl group; (iii) a group —OR$^5$, wherein R$^5$ is an unsubstituted alkyl, alkenyl or alkynyl group containing up to 6 carbon atoms; a C$_{1-16}$ alkyl group carrying a group R$^6$CO$_2$— or R$^6$O— where R$^6$ is a C$_{1-4}$ alkyl group, or carrying a C$_{2-6}$ alkanoyl, carboxyl, C$_{2-6}$ alkoxycarbonyl or cyano group; a hydroxyalkyl group having 2–6 carbon atoms; a 4-nitrobenzyl, benzyl, phenethyl, phenyl or tetrahydropyranyl group; or a cycloalkyl group having 3–7 carbon atoms optionally carrying a C$_{1-4}$ alkoxy group; (iv) a group —OR$^7$ wherein R$^7$ represents a group R$^8$CO— wherein R$^8$ is a C$_{1-8}$ alkyl, C$_{2-8}$ alkenyl, or C$_{3-12}$ cycloalkyl group, which R$^8$ group may be substituted by a hydroxyl, C$_{1-4}$ alkoxy, phenoxy, cyano or amino group or R$^8$ is a benzyl, thienylmethyl, phenyl, thienyl, α-benzyloxycarbonylbenzyl, α-phenoxycarbonylbenzyl or α-aminobenzyl group; (v) a group O.-CONR$^9$R$^{10}$ wherein R$^9$ and R$^{10}$, which may be the same or different, represent hydrogen; C$_{1-5}$ alkyl; C$_{2-6}$ alkanoyl, or a benzyl or phenyl group; (vi) a group OCSNHR$^9$ wherein R$^9$ is as hereinbefore defined other than hydrogen; (vii) the residue of a sulphur nucleophile represented by —SH, —SR$^{11}$, —SOR$^{11}$ or —SC(=YR$^{12}$ wherein R$^{11}$ represents an alkyl, alkenyl or alkynyl group of up to 6 carbon atoms or a benzyl, phenyl or pyridyl group, all such groups R$^{11}$ being unsubstituted or carrying a substituent selected from the group consisting of hydroxy, a group —OR$^6$ or R$^6$CO$_2$—, where R$^6$ is as hereinbefore defined, carboxyl, amino, cyano, a group of formula —COOR$^{15}$ where R$^{15}$ is C$_{1-4}$ alkyl, and a group of formula —NR$^{13}$R$^{14}$ where R$^{13}$ and R$^{14}$, which may be the same or different, represent hydrogen or C$_{1-4}$ alkyl; and R$^{12}$ is a group as defined for R$^{11}$, or is a group —OR$^{11}$, —SR$^{11}$ or —NR$^{13}$R$^{14}$ where R$^{13}$ and R$^{14}$ are as hereinbefore defined; and Y represents oxygen or sulphur; or (viii) a group OR$^5$ wherein R$^5$ represents a silyl group carrying three substituents which may be the same or different C$_{1-4}$ alkyl groups, wherein all substitution is monosubstitution.

2. 1-(4-Nitrobenzyloxycarbonyl)-1-(2-oxo-4-triethylammonioazetidin-1-yl)but-1-en-2-olate.

3. 4-(1-Ethoxyethoxy)-1-(4-nitrobenzyloxycarbonyl)-1-(2-oxo-4-triethylammonioazetidin-1-yl)but-1-en-2-olate.

4. The salt of a compound of claim 1 formed with citric, formic, tartaric, acetic, p-toluenesulphonic, nitric, hydrochloric, sulphuric or perchloric acid.

5. The compound of claim 1 wherein R$^5$ represents a methyl, ethyl, propyl, butyl, allyl, propargyl, hydroxyethyl, 1-ethoxyethyl, phenyl, benzyl, phenethyl, cyclohexyl, t-butyldimethylsilyl or tetrahydropyranyl group;

R$^8$ represents a methyl, ethyl, propyl, butyl or amyl group, a benzyl group, a phenyl group; or NR$^9$R$^{10}$ represents a methylamino or anilino group;

R$^{11}$ represents a methyl, ethyl, propyl, butyl, allyl, propargyl, hydroxyethyl, ethoxyethyl, phenyl, benzyl, cyclohexyl or pyridyl group; and R$^{12}$ C=Y represents an ethoxythiocarbonyl, carbamoyl, thiocarbamoyl, dimethylthiocarbamoyl, thiobenzoyl, thioacetyl, or acetyl group.

6. The compound of claim 1 wherein R$^{16}$ is a p-nitrobenzyl or benzyl group.

7. A compound as claimed in claim 1 in crystalline form.

* * * * *